United States Patent [19]

Cohen et al.

[11] Patent Number: 4,745,182

[45] Date of Patent: May 17, 1988

[54] HERPES VIRUS SPECIFIC IMMUNOLOGICAL MATERIALS AND METHODS

[75] Inventors: Gary H. Cohen, Havertown, Pa.; Roselyn J. Eisenberg, Haddonfield, N.J.

[73] Assignee: University Patents, Inc., Westport, Conn.

[21] Appl. No.: 696,582

[22] Filed: Jan. 31, 1985

Related U.S. Application Data

[63] Continuation-in-part of Ser. No. 644,205, Aug. 24, 1984, abandoned.

[51] Int. Cl.$^4$ .............. C07K 15/00; C12P 21/00; C12N 15/00; G01N 33/571
[52] U.S. Cl. ................................ 530/387; 530/808; 530/809; 530/810; 530/811; 435/172.2; 435/240; 435/68; 435/70; 435/948; 436/548; 436/511; 424/85; 424/89; 424/86; 935/103; 935/106; 935/110
[58] Field of Search ............ 435/172.2, 948, 240, 435/68, 70; 436/548, 511; 424/89, 86, 85; 530/387, 808, 809, 810, 811; 935/103, 106, 110

[56] References Cited

U.S. PATENT DOCUMENTS

| | | | |
|---|---|---|---|
| 4,430,437 | 2/1984 | Hampar et al. | 424/85 |
| 4,535,057 | 8/1985 | Drissman et al. | 435/810 |
| 4,572,896 | 2/1986 | Hampar et al. | 435/68 |
| 4,618,570 | 10/1986 | Burke et al. | 435/68 |

OTHER PUBLICATIONS

Cohen et al., *J. Virol.*, 49, 1984, pp. 102–108.
Eisenburg et al., *J. Viol.*, 41, 1982, pp. 478–488.
Eisenburg et al., *J. Viol.*, 41, 1982, pp. 1099–1104.
Holland et al., *J. Virol.*, 45, 1983, pp. 672–682.
Pereira et al., *Inf. and Immunity*, 35, 1982, pp. 363–367.
Pereira et al., Chapter 6, pp. 119–138, Monoclonal Hybridoma ed Hurrell (CRC), 1982.
Kennedy et al., *J. Immunol*, 130, 1983, pp. 1943–1946.
Arvin et al., *Inf. and Immunity*, 40, 1983, pp. 184–189.

*Primary Examiner*—John Kight
*Assistant Examiner*—Garnette D. Draper
*Attorney, Agent, or Firm*—Marshall, O'Toole, Gerstein, Murray & Bicknell

[57] ABSTRACT

Disclosed are antibody substances displaying unique, multi-specific immunoreactivities with respect to glycoprotein D of Herpes Simplex Virus types 1 and 2 (HSV gD-1 and gD-2) and structurally related compounds. Illustratively, an IgG Type 2 monoclonal antibody material produced by mouse-mouse hybridoma cell line A.T.C.C. No. HB8606 is capable of in vitro neutralization of HSV-1 and HSV-2 infectivity and of specific immunological reactivity and reversible immunobinding with natrually-occuring and recombinant gD-1 and gD-2 in both native and denatured conformations as well as with proteinaceous materials (produced, e.g., by proteolytic digestion of naturally-occurring materials, by recombinant methods, or by polymerization of amino acids) which comprise a primary structural conformation substantially duplicating part or all of that which is predicted to be extant at residues 266 through 287 of gD-1 and gD-2 [i.e., PELA(or V)PEDPED-SALLEDPV(or A)GTVA(or S)]. Disclosed also are novel procedures for detection, quantification and isolation by affinity purification of gD-1, gD-2 and structurally related compounds.

14 Claims, No Drawings

HERPES VIRUS SPECIFIC IMMUNOLOGICAL MATERIALS AND METHODS

This application is a continuation-in-part application of our co-pending U.S. Patent Application Ser. No. 644,205, filed Aug. 24, 1984 now abandoned.

BACKGROUND

The present invention relates to antibody substances and more particularly to antibody substances displaying unique, multi-specific immunoreactivities with respect to glycoprotein D of Herpes Simplex Virus types 1 and 2 (HSV gD-1 and gD-2) and structurally related compounds.

In the recent past, substantial research efforts have been directed to the isolation and characterization of the Herpes Simplex Virus glycoproteins which constitute structural components of the virion envelope and are likely to play an important role in initiation of viral infection. Among the more significant advances based upon this research is the discovery by the present applicants of novel preparations of HSV glycoprotein D which, when employed as the active immunogen of vaccine compositions, provoke significant protection against HSV infection and applicants further discovery of immunologically significant polypeptides which duplicate or substantially duplicate continuous sequences of amino acids extant in HSV gD. Incorporated by reference herein for the purpose of providing background information with respect to the art are the disclosures of applicants' co-pending U.S. Patent Application Ser. No. 463,141, filed Feb. 4, 1983, and entitled "Methods and Materials for Herpes Simplex Virus Vaccination". (See, also, International Patent Application W083/02897, published Sept. 1, 1983.)

Research in characterization of HSV gD-1 and gD-2 has been substantially assisted by the results obtained through application of recombinant DNA techniques to the cloning and expression in microbial hosts (e.g., bacteria, yeast and mammalian cells in culture) of DNA sequences coding for part or all of the polypeptide sequences of gD-1 and gD-2. DNA sequencing of genes coding for the proteins has resulted in prediction of their primary structural conformation (amino acid sequence). See, e.g., Watson, et al., *Science*, 218, pp. 381–384 (1982) providing the predicted sequence for gD-1 including both a "leader" region and a region designated as that of the "mature" protein. Similar recombinant methods have allowed the prediction of the gD-2 sequence and the comparison thereof with gD-1. Also specifically incorporated herein by reference, therefore, are the disclosures of Watson, *Gene*, 26, pp. 307–312 (1983) which generally provide information as set forth below in Table I concerning the comparative primary structural conformation (amino acid sequences) predicted for "mature" HSV gD-1 and gD-2 based on DNA sequencing.

In the Table and throughout, the following single and triple letter "codes" for amino acid residues will be employed: A=Ala=Alanine; C=Cys=Cysteine; D=Asp=Aspartic Acid; E=Glu=Glutamic Acid; F=Phe=Phenylalanine; G=Gly=Glycine; H=His=Histidine; I=Ile=Isoleucine; K=Lys=Lysine; L=leu=Leucine; M=Met=Methionine; N=Asn=Asparagine; P=Pro=Proline; Q=Gln=Glutamine; R=Arg=Arginine; S=Ser=Serine; T=Thr=Threonine; V=Val=Valine; W=Trp=Tryptophan; and Y=Tyr=Tyrosine.

TABLE I

```
     1
gD-1 KYALADASLKMADPNRFRGKDLPVLDQLTDPPGVRRVYHI              40
gD-2 ------------- P-----------------------N-------------------------K-----------
gD-1 QAGLPDPFQPPSLPITVYYAVLERACRSVLLNAPSEAPQI              80
gD-2 -- PS --E ---------------I------------------------------H-----------------
gD-1 VRGASEDVRKQPYNLTIAWFRMGGNCAIPITVMEYTECSY             120
gD-2 ------------DEA---HT----------------Y--------D-----------------------------P---
gD-1 NKSLGACPIRTQPRWNYYDSFSAVSEDNLGFLMHAPAFET             160
gD-2 ----------V--------------------S-------------------------------------------------
gD-1 AGTYLRLVKINDWTEITQFILEHRAKGSCKYALPLRIPPS             200
gD-2 ---------------------------------------------RA-----------------------A
gD-1 ACLSPQYQQGVTVDSIGMLPRFIPENQRTVAVYSLKIAG              240
gD-2 -------TSK-----------------------------------------------L----------------
gD-1 WHGPKAPYTSTLLPPELSETPNATQPELAPEDPEDSALLE             280
gD-2 ---------------P-----------------------D-T----------------V-------------------------
gD-1 DPVGTVAPQIPPNWHIPSIQDAATPYHPPATPNNMGLIAG             320
gD-2 ----A--------SS--------------------------V-------H--A----A--S - P------I----  319
gD-1 AVGGSLLAALVICGIVYWMHRRTRKAPKRIRLPHIREDDQ             360
gD-2 -- LA ---- T ------------G----AF---VR-----AQM----------L------------D-----A  359
gD-1 PSSHQPLFY                                            369
gD-2 --P---------------                                    368
```

Briefly summarized, mature forms of gD-1 and gD-2 are predicted to consist of 369 and 368 amino acid residues, respectively, with gD-2 "lacking" a residue corresponding to residue 304 of gD-1, and with approximately 85% homology existing between the two sequences. See, also, Lasky, et al., *DNA*, 3, pp. 23–29 (1984) and Rawls, et al., *J. Virol.*, 51, pp. 263–265 (1984).

Companion research in the characterization of HSV gD-1 and gD-2 has been directed to the localization of antigenic determinants of these materials [see, Eisenberg, et al., *J. Virol.*, 41, pp. 1099–1104 (1982), Cohen, et al., *J. Virol.*, 49, pp. 102–108 (1984), Eisenberg, et al., *J. Virol.*, 49, pp. 265–268 (1984) and references cited therein] through the use of typespecific and type-common monoclonal antibody substances. The essentially dual goals of this work have been the ascertaining of one or more determinants which stimulate production of neutralizing antibodies in HSV hosts and the identification of antibody substances correspondingly useful in detection, quantification, and affinity purification of such immunologically significant substances.

Despite the above-noted advances in the art, there continues to exist a need for antibody substances useful in the detection, quantification and isolation by affinity purification from natural and recombinant sources of gD-1, gD-2 and structurally related compounds such as gD-1 and gD-2 fragments and/or analogs.

BRIEF SUMMARY

The present invention provides novel antibody substances displaying unique, multi-specific immunoreactivities with respect to glycoprotein D of Herpes Simplex Virus types 1 and 2 (HSV gD-1 and gD-2) and structurally related compounds, as well as novel procedures and materials for detection, quantification and isolation by affinity purification of gD-1, gD-2 and structurally related compounds.

Antibody substances of the present invention are characterized, inter alia, by type common binding to both gD-1 and gD-2 in both native and denatured states, indicating that the antibodies bind to the same or essentially the same epitope within the two glycoproteins and that the epitope bound is a linear rather than conformational epitope. Antibody substances of the invention are further characterized by reversible immunobinding to proteinaceous materials which include all or an immunologically significant part of the continuous sequence of amino acid residues spanning residues 266 through 287 of the predicted sequence for gD-1 and gD-2, i.e., PELA(or V)PEDPEDSALLEDPV(or A)GTVA(or S). In preferred forms, antibody substances of the invention comprise monoclonal antibodies produced by hybridoma cell lines.

Illustratively provided according to the present invention are monoclonal antibodies produced by mouse-mouse hybridoma cell line A.T.C.C. No. HB8606, deposited Oct. 26, 1984 with the American Type Culture Collection, 12301 Parklawn Drive, Rockville, Maryland 20852, in accordance with the U.S. Patent and Trademark Office's requirements for microorganism deposits.

Among the presently preferred embodiments of the invention is the IgG monoclonal antibody designated "DL-6" which is produced by hybridoma cell line A.T.C.C. No. HB8606. This antibody is characterized by: (a) capacity to bind protein A; (b) capacity to neutralize in vitro infectivity of HSV-1 and HSV-2; (c) specific immunological reactivity with, and capacity to reversibly immunobind to, naturally occurring and recombinant gD-1 and gD-2 in native and denatured conformations whether glycosylated or not; and (d) specific immunological reactivity with, and capacity to reversibly immunobind to, proteinaceous materials including all or a substantial, immunologically significant, part of an amino acid sequence duplicative of that predicted to be extant at residues 266 through 287 of gD-1 and gD-2, i.e., PELA(or V)PEDPEDSALLEDPV(or A)GTVA(or S). Among the proteinaceous materials herein specifically noted to be immunoreactive with antibody DL-6 are gD-1 fragments produced by recombinant methodologies such as the nonglycosylated fragment "8-300[1]" produced in transformed E.coli cells, a glycosylated "1-287[1]" fragment produced in Hep-2 cells, a "-5-369[1]product produced in E.coli cells, and synthetic peptides "266-279[1]", "266-279[2]" and "268-287[1]" produced by polymerization of amino acids. Non-immunoreactive with antibody DL-6 are recombinant-produced gD-1 fragments such as the glycosylated fragment "1-275[1]" produced in CHO cells, synthetic peptides duplicative of various portions of the initial 23 residues of the amino terminal of gD-1 and gD-2 and "hybrids" thereof, and a synthetic peptide "340-356[1]" which duplicates the predicted primary structural conformation of residues 34 through 356 for gD-1.

Use of antibody DL-6 in affinity purification of gD-1 from natural sources has proven to be highly efficient, providing yields of immunologically active gD-1 preliminarily determined to be in two- to threefold excess of those obtained using prior monoclonal anti-gD antibody preparation. Infected cell culturederived gD-1 so isolated has preliminarily been shown to be at least as active a protective immunogen as previously isolated materials.

Other aspects and advantages of the present invention will be apparent upon consideration of the following detailed description of presently preferred embodiments.

DETAILED DESCRIPTION

The following examples illustrate practice of the invention in the production of hybridoma cell line A.T.C.C. No. HB8606. Also illustrated is the characterization, amplification and determination of the properties of the monoclonal antibodies produced by these cell lines, with specific emphasis on the immunological properties and uses of presently preferred antibody "DL-6" produced by hybridoma cell line A.T.C.C. No. HB 8606.

More specifically, Example 1 relates to the general methods and materials variously employed in the subsequent examples. Example 2 relates to stimulation of a mouse toward production of polyclonal antibodies to gD-1; fusion of mouse spleen cells with mouse myeloma cells; and the screening, cloning and growth of hybridoma cells comprising the cell line A.T.C.C. No. HB8606. Example 3 relates to preliminary screening of immunoreactivity of monoclonal antibodies produced by the four above-noted cell lines. Example 4 relates to more extensive screening of monoclonal antibody DL-6 which serves to more fully establish its immunological characteristics and the nature of the epitope with which it binds. Example 5 relates to preliminary practice of procedures for use of antibody DL-6 in the affinity purification of gD-1 from natural sources.

EXAMPLE 1

A. Cells, Virus and Radioactive Labelling Procedures

The general conditions employed in the growth and maintenance of BHK and KB cells and for the propagation of virus were as described in Cohen, et al., *J. Virol.*, 14, pp. 20–25 (1972) and Cohen, et al. *J. Virol.*, 10, pp. 1021–2030 (1974). For infection, an input multiplicity of 20 pfu for HSV-1 (strain HF) and 10 pfu of HSV-2 (strain Savage) were used. Procedures for labelling of HSV infected cells with [35S]-methionine (specific activity 600 Ci/mmol) and [2,3-3H]-arginine (specific activity 15 Ci/mmol) were as described in Cohen, et al., *J. Virol.*, 27, pp. 172–181 (1978); Eisenberg, et al., *J. Virol.*, 31, pp. 608–620 (1979); Eisenberg, et al., *J. Virol.*, 41, pp. 478–488 (1982); and Eisenberg, et al., *J. Virol.*, 35, pp. 428–435 (1980).

B. Monoclonal Antibodies

Monoclonal antibodies ("MCAb's") employed for comparative purposes in the following examples were as follows: MCAb HD-1 (Group I) and MCAb 170 (Group VII) were as according to Periera, et al. *Infect. & Immun.*, 35, pp. 363–367 (1982) and Eisenberg, et al., *J. Virol.*, 41, pp. 478–488 (1982). MCAb's 55S, 57S (Group V), 11S (Group III), 41S (Group IV) and 45S (Group VI) were as described in Showalter, et al., *Infect. & Immun.*, 34, pp. 684–692 (1981).

C. Synthetic Peptides

Synthetic peptides employed in screening antibody reactivities to peptides based on residues within positions 1–23 of gD-1 and gD-2 were prepared as in Cohen, et al., *J.Virol.*, 49, pp. 102–108 (1984). Synthetic peptides 340–356[1] with cysteine added to the amino terminal, and 268–287[1], with cysteine added to the carboxy terminal, were prepared by Peninsula Labs., Inc. Synthetic peptides 266–279[1] and 266–279[2] may be prepared according to such well known solid phase procedures as those of Merrifield, *J.Am.Chem.Soc.*, 85, pp. 2149–2154 (1963). Procedures for coupling peptides to keyhole limpet hemocyanin (KLH) were generally as described in Liu, et al. *Biochemistry*, 18, pp. 690–697 (1979). For use in immunoblot assays, peptides were dissolved in 0.1 M Tris, pH 7.8, 0.15 M HCl.

D. Preparation of Native and Denatured gD

Unless otherwise indicated, gD-1 and gD-2 were purified from cytoplasmic extracts of infected cells by affinity chromatography using MCAb HD-1 as described in Eisenberg, et al., 41, pp. 478–488 (1982). Proteins eluted from the immunoadsorbent column with KSCN and dialyzed against 0.01 M Tris, pH 7.5, 0.15 M NaCl, 0.1% Nonidet-P40 (NP-40) (TSN buffer) were designated as being in "native" conformation. For preparation of denatured materials, purified gD-1 or gD-2 were suspending in disrupting buffer to yield a final concentration of 3% SDS, 100 mM Tris, pH 7.0, 10% 2-mercaptoethanol and 0.5% glycerol. The sample was boiled for 5 minutes. Iodoacetamide (0.1 M in 0.1 M Tris pH 8.0) was added to give a final concentration of 33 mM iodoacetamide and the mixture was incubated for 1 hour at room temperature. Samples were dialyzed extensively against TSN buffer.

E. Recombinant gD Materials

1. A first truncated glycoprotein ("1-275[1]") comprising residues 1-275 predicted for mature gD-1 was prepared according to the procedures described in Lasky, et al., *Biotechnology*, 2, pp. 527–532 (1984) as a secretion product of transformed Chinese Hamster Ovary cells and was purified by affinity chromatography according to Eisenberg, et al., *J.Virol.*, 41, 1099-1104 (1982).

2. A second truncated glycoprotein ("1-287[1]") comprising the fusion product of residues 1-287 predicted for gD-1 and 48 carboxy terminal residues of HSV thymidine kinase (TK) was prepared according to the procedures of Gibson, et al. *J.Cell.Biochem.*, Supp. 8B (1984) Abstracts, 13th Annual U.C.L.A. Symposia, #1337, p. 191 [and see also, Gibson, et al., *J.Virol.*, 48, pp. 396–404 (1983)] as a secretion product of virally infected Hep-2 cells. Briefly, the virus vector included a truncated form of the gD-1 gene (extending from the SacI site upstream of the gene to the NarI site at residue 287 which was inserted into the BglII site of the TK gene. The protein was affinity purified using McAb II-436-1 as described in Noble, et al., *J.Virol.*, 129, 218-224 (1983).

3. A third truncated polypeptide ("8-300[1]") comprising residues of 8 to (about) 300 was produced in *E.coli* according to the general procedures set out in Watson, et al., *Science*, 218, pp. 381–384 (1982).

4. A fusion polypeptide ("-5-369[1]") comprising residues spanning positions -5 through 369 of gD-1 with 11 amino terminal residues of β-galactosidase was obtained upon transformation of *E.coli* host cells with an M13 mp8 viral vector into which had been inserted a NcoI through NruII gD-1 gene fragment according to Watson, et al., *Science*, supra, at a site within a β-galactosidase gene present in the vector.

F. Immunoprecipitation and SDS-PAGE

Glycoprotein D was immunoprecipitated from HSV-1 or HSV-2 infected cell extracts (cells infected for 6 hours) using antisera or MCAb and *Staphylococcus aereus* protein A (IgG Sorb, New England Enzyme Center). SDS-PAGE was carried out in slabs of 10% acrylamide cross-linked with 0.4% N,N'diallyltartardiamide (DATD), as described in Eisenberg, et al., *J.Virol.*, 31, pp. 608-620 (1979) and Watson, *Gene*, 26, pp. 307-312 (1983). For autoradiography, gels were dried on filter paper and placed in contact with Kodak XAR-5 film. For fluorography, the gels were treated with Amplify (Amersham), dried on filter paper and exposed to Kodak XAR-5 film at −70° C.

G. Immunoblot and Neutralization Assays

The immunoblot assays were done as described in Cohen, et al., *J.Virol.*, 49, pp. 102-108 (1984) and Hebrink, et al., *J.Immunol.Methods*, 48, pp. 672-682 (1983). Virus neutralization assays (50% plaque reduction method) using HSV-1 (HF) or HSV-2 (Savage) were carried out as described in Cohen, et al., *J.Virol.*, 47, pp. 172-11 (1978) and Cohen, et al. *J.Virol.* 10, pp. 1021-2040 (1972).

EXAMPLE 2

Mouse-mouse hybridoma cell lines were obtained according to the following procedure. BALB/c mice were hyperimmunized with affinity purified gD-1 of Example I, with an initial 6 μg dose of gD-1 administered intraperitoneally [see, Long, et al., *Infect. Immun.*, 37, pp. 761-764 (1984)]. Three days after an intravenous boost comprising 1 μg of the immunogen, spleens were removed and cells were fused to BALB/c SP2/0 cells using a PEG-fusogen by the method of McKearn, pp. 368-369 in Kennett, et al., "Monoclonal Antibodies Hybridomas: A New Dimension In Biological Analysis", Plenum Press, New York, N.Y. (1980). Supernatants from wells containing viable cell colonies after HAT treatment were screened for the presence of gD-specific antibodies by immunoblot procedures. Cells positive for gD-1 and gD-2 were subcloned and a representative cell line, producing monoclonal antibody "DL-6" was deposited with the A.T.C.C. as No. HB8606. Monoclonal antibodies may be isolated from culture fluids of growth of these four cell lines by AMICON filtration concentration followed by precipitation with ammonium sulfate. Alternatively the concentrated culture fluids may be adsorbed to Protein A Sepharose columns (Pharmacia Corp.). As another alternative, monoclonal antibodies may be prepared in amplified form by the ascites method as generally described at page 403 of the Kennett, et al., text, supra. Briefly, about $3 \times 10^6$ to $3 \times 10^7$ hybridoma cells are injected into peritoneal cavities of BALB/c mice primed with 0.25 ml Pristane. Antibodies may be isolated from ascites fluid by ammonium sulfate precipitation and DEAE Sephadex as in Eisenberg, et al. *J.Virol.*, 41, pp. 1099-1104 (1982). To prepare immunoadsorbent columns, isolated IgG type 2 antibodies may be linked to cyanogen bromide-activated Sepharose 4B columns, typically in amounts ranging from 5-12 mg of IgG per gram of Sepharose. Purified antibodies may be iodinated with 125I by the chloramine T method of Greenwood, et al., *Biochem.J.*, 89, pp. 114-123 (1963) or, preferably, by the lactoperoxidase method of Liu, et al., supra.

EXAMPLE 3

Monoclonal antibody DL1-6 was preliminarily screened in immunoblot assays against purified gD and subsequently was found to be immunoreactive with native and denatured gD-1 and gD-2 but not with the recombinant glycoprotein 1-275[1], indicating that the type-common epitope recognized was not the sequential epitope (Group V) projected to exist between residues 340-356 of gD-1 and gD-2.

Based on the absence of binding to synthetic peptides duplicating residues 1-23 of gD-1 and gD-2, antibody recognition of the (Group VII) sequential epitope in that region was ruled out. DL-6 monoclonal antibodies produced in A.T.C.C. No. HB8606 culture fluids and as amplified by the ascites method were employed in more extensive screening procedures as set out in the following example.

EXAMPLE 4

Antibody DL-6 was tested in a fluorescent antibody assay on infected cells and revealed type-common membrane immunofluorescence, indicating that the epitope of gD-1 and gD-2 recognized was available for binding on the glycoproteins when glycoproteins were inserted in the cell membrane.

Neutralization assays (in vitro) revealed that the DL-6 antibody neutralized HSV-1 at a 1:50 dilution and HSV-2 at a 1:20 dilution, employing a 50% endpoint as in Eisenberg, et al., *J. Virol.*, 41, pp. 1099-1104 (1982).

Immunoblot assays were employed to screen for binding to a variety of synthetic peptides listed in Table II below. In the Table, the sequence of amino acids in the peptides tested is represented by the initial two numbers and the bracketed number indicates type specificity of the sequence. A bracketed H indicates that the sequence is a hybrid of the projected type 1 and type 2 sequences.

Immunoblot assay results employing the Table II peptides revealed no immunoreactivity for DL-6 with peptides (a) through (l) or (p) but significant reactivity with peptides (m), (n) and (o), representing residues 266-279 of gD-1 and gD-2 and 268-287 of gD-1.

Because DL-6 immunoblot assays revealed significant reactivity with gD-1 and gD-2 present in gross precipitates obtained from HSV-1 and HSV-2 infected cells grown in the presence of tunicamycin, involvement of carbohydrates in the epitope recognized by DL-6 was ruled out.

Immunoreactivity of DL-6 with various glycoprotein D-like fragment and analog materials produced by recombinant methods was determined by immunoblot. As mentioned previously, DL-6 was essentially non-reactive with the recombinant glycoprotein 1-275[1] produced by the Lasky, et al. procedure, supra. DL-6 was immunoreactive, however, with every recombinant product tested which included a sequence of amino acid residues spanning projected residues 266-287 of gD-1, i.e., the recombinant 1-287[1], the recombinant 8-300[1], and the recombinant -5-396[1] described in Example 1.

Based on the immunoreactivity "profile" generated by the above testing, the following conclusions can be proposed concerning the epitope recognized by antibodies of the invention as represented by antibody DL-6. The antibody recognized both gD-1 and gD-2 in native, denatured and non-glycosylated forms, indicating that the epitope comprises a type-common or essentially type-common continuous sequence of amino acid residues. The antibody recognized all recombinant gD-1 replicas and analogs including the projected continuous sequence of residues 266-287 of gD-1. Lack of recognition of the recombinant glycoprotein 1-275[1] indicates that at least some residues beyond predicted residue 275 are significant to recognition of the epitope (and, by correlation with reactivity with the peptide 266-279[1], possibly four or more additional residues may be involved). On the other hand, the gD-1 and gD-2 type-common recognition capacity of the antibody, when correlated with the type-specific nature of the 266-279[1], 266-279[2] and 268-287[1] reactive peptides, indicates that the epitope recognized includes, or is included in, the type-common sequence which is common to the synthetic peptides, i.e., the sequence comprising the predicted residues 270-279, PEDPEDSALL.

TABLE II

| Peptide | Amino Acid Sequence |
|---|---|
| (a) 1-23[1] | K Y  A L A  D A  S L K  M  A D P N  R F R G K  D L P |
| (b) 1-23[2] | K Y  A L A  D P  S L K  M  A D P N  R F R G K  N L P |
| (c) 1-23[H] | K Y  A L A  D P  S L K  M  A D P N  R F R G K  D L P |
| (d) 1-16[1] | K Y  A L A  D A  S L K  M  A D P N  R |
| (e) 1-16[2] | K Y  A L A  D P  S L K  M  A D P N  R |
| (f) 3-23[H] | A L A  D P  S L K  M  A D P N  R F R G K  D L P |
| (g) 8-23[1] | S L K  M  A D P N  R F R G K  D L P |
| (h) 8-23[2] | S L K  M  A D P N  R F R G K  N L P |
| (i) 12-23[1] | M  A D P N  R F R G K  D L P |
| (j) 13-23[2] | A D P N  R F R G K  N L P |
| (k) 17-23[1] | R F R G K  D L P |
| (l) 17-23[2] | R F R G K  N L P |
| (m) 266-279[1] | P E L A P E D P E D S A L L |
| (n) 266-279[2] | P E L V P E D P E D S A L L |
| (o) 268-287[1] | L A P E D P E D S A L L E D P V G T V A |
| (p) 340-356[1] | H R R T R K A P K R I R L P H I R |

The foregoing example serves to illustrate the manifest value of the highly specific monoclonal antibodies of the invention in detection and quantification of gD-1, gD-2 and structurally related compounds including peptides and proteinaceous materials which include a continuous sequence of amino acid residues duplicative in whole or in part of those projected to be extant as residues 266–287 of gD-1 and gD-2. The following illustrative example relates to studies of antibodies of the invention in the context of generally ascertaining their degree of affinity for gD-1, gD-2 and structurally related compounds vis-a-vis antibodies heretofore developed.

EXAMPLE 5

Ascites-derived antibody DL-6 was adsorbed on a cyanogen bromide-activated Sepharose 4B column as previously described and employed in the isolation by affinity purification of gD-1 from infected cells. Employing equivalent conditions, the DL-6 antibody column was able to bind from two to three fold more of the target glycoprotein than columns wherein the (Group I) MCAb HD-1 was employed. Furthermore, preliminary vaccination studies on mice which employed the DL-6 affinity purified materials as the active immunogen revealed that the material was at least as active as HD-1 affinity purified material in provoking an immune response protective against a lethal viral challenge.

A "competition" assay was performed wherein monoclonal antibodies DL-6, HD-1, 11S, 45S, and 170 (100–200 μl, representing 150 to 600μg of IgG) were linked to a Sepharose 4B column and the column was used to adsorb cytoplasmic extracts of HSV-1 infected cells (100 μl extract incubated at 37° C. for 2 hours). The immunoadsorbents were washed ten times with buffer and an iodinated second antibody (ca. 250,000 cpm) was added. After extensive washing, the columns were counted with a gamma counter. Theoretically, because an excess of antibody was employed on the column, no labelled antibody of the same type should be adsorbed to the column. Of all antibodies tested against their labelled counterparts, DL-6 displayed the highest capacity to bind gD-1 to the exclusion of its labelled counterpart.

The foregoing illustrative examples relate to monoclonal antibody-producing hybridoma cell lines formed by means of standard, chemically facilitated fusions of mouse spleen and tumor cells. It will be understood that a variety of hybridoma cell producing techniques may be alternatively applied to cells of differing mammalian species origins to provide hybridoma cell lines of the present invention which are capable of producing antibodies specifically immunologically reactive with gD-1, gD-2 and structurally related compounds including the amino acid sequence, RNHPEDPEDSALLCOR′, wherein R and R′ are the same or different amino acid residues or R is hydrogen or R′ is hydroxyl. Specifically comprehended by the invention, therefore, are hybridoma cell lines formed by genetic fusion of human, rat or other mammalian species cell materials (or interspecies mixtures thereof), whether the fusion is performed through chemical or electrical mediation and involves whole cells or genetically significant fragments thereof. Similarly, while the immunogen employed in development of hybridomas of the foregoing illustrative examples was affinity purified gD-1 derived from natural sources, a variety of immunogens may serve as suitable replacements therefor. Typical substitutes would include gD-2 as well as gD-1 and gD-2 polypeptide replicas in native and denatured form produced by recombinant methods in suitable microbial hosts such as bacteria, yeast and mammalian cells in culture and provided in glycosylated or non-glycolsylated forms, with or without additional amino or carboxy terminal amino acid residues. Other preferred substitutes would include synthetic peptides duplicating all or a substantial, immunologically significant portion of the sequence of amino acid residues present at positions 266–287 of gD-1 or gD-2, such as the continuous sequence of RNHPEDPEDSALLCOR′, wherein R and R′ are the same or different amino acid residues or R is hydrogen or R′ is hydroxyl.

Numerous modifications and variations in the invention as described in the above illustrative examples are expected to occur to those skilled in the art and consequently only such limitations as appear in the appended claims should be placed thereon.

What is claimed is:

1. A monoclonal antibody capable of specifically binding with glycoprotein D of Herpes Simplex Virus types 1 and 2 and with a proteinaceous material comprising an amino acid sequence duplicating part or all of the following sequence:

PELA(or V)PEDPEDSALLEDPV(or A)GTVA(or S).

2. A monoclonal antibody according to claim 1 capable of specifically binding with a proteinaceous material comprising the following amino acid sequence:

PELA(or V)PEDPEDSALL.

3. A monoclonal antibody according to claim 1 capable of specifically binding with a proteinaceous material comprising the following amino acid sequence:

LA(or V)PEDPEDSALLEDPV(or A)GTVA(or S).

4. A monoclonal antibody according to claim 1 capable of specifically binding with a proteinaceous material comprising the following amino acid sequence:

PEDPEDSALL.

5. A hybridoma cell line capable of producing a monoclonal antibody capable of specifically binding with glycoprotein D of Herpes Simplex Virus types 1 and 2 and with a proteinaceous material comprising an amino acid sequence duplicating part or all of the following sequence: PELA(or V)PEDPEDSALLEDPV(or A)GTVA(or S).

6. A hybridoma cell line according to claim 5 derived from murine or human cells.

7. A hybridoma cell line according to claim 5 which is A.T.C.C. No. HB8606.

8. A monoclonal antibody produced by hybridoma cell line ATCC No. HB8606.

9. In an immunological procedure for isolation of glycoprotein D of Herpes Simplex Virus Type 1 or Type 2 or immunologically active fragments or analogs thereof on the basis of a selective immunological reaction with an anitbody specific therefor, the improvement comprising employing a monoclonal antibody capable of specifically binding with glycoprotein D of Herpes Simplex Virus types 1 and 2 and with a proteinaceous material comprising an amino acid sequence duplicating part or all of the following sequence:

PELA(or V)PEDPEDSALLEDPV(or A)GTVA(or S).

10. In an immunological procedure for isolation or glycoprotein D of Herpes Simplex Virus Type 1 or Type 2 or immunologically active fragments or analogs thereof on the basis of a selective immunological reaction with an antibody specific therefor, the improvement comprising employing a monoclonal antibody produced by hybridoma cell line A.T.C.C. No. HB8606.

11. In an immunological procedure for quantitative detection of glycoprotein D of Herpes Simplex Virus Type 1 or Type 2 or immunologically active fragments or analogs thereof on the basis of a selective immunological reaction with an antibody specific therefor, the improvement comprising employing a monoclonal antibody capable of specifically binding with glycoprotein D of Herpes Simplex Virus types 1 and 2 and with a proteinaceous material comprising an amino acid sequence duplicating part or all of the following sequence:

PELA(or V)PEDPEDSALLEDPV(or A)GTV-A(or S).

12. In an immunological procedure for quantitative detection of glycoprotein D of Herpes Simplex Virus Type 1 or Type 2 or immunologically active fragments or analogs thereof on the basis of a selective immunological reaction with an antibody specific therefor, the improvement comprising employing a monoclonal antibody produced by hybridoma cell line A.T.C.C. No. HB8606.

13. An immunoadsorbent for use in the affinity purification of glycoprotein D of Herpes Simplex Virus type 1 or 2 or other proteinaceous materials including part or all of the following sequence of amino acids:

PELA(or V)PEDPEDSALLEDPV(or A)GTV-A(or S), said immunoadsorbent comprising a solid support having bound thereto a monoclonal antibody capable of specifically binding with glycoprotein D of Herpes Simplex Virus types 1 and 2 and with a proteinaceous material comprising an amino acid sequence duplicating part or all of the following sequence:

PELA(or V)PEDPEDSALLEDPV(or A)GTV-A(or S).

14. An immunoadsorbent for use in the affinity purification of glycoprotein D of Herpes Simplex Virus type 1 or 2 or other proteinaceous materials including part or all of the following sequence of amino acids:

PELA(or V)PEDPEDSALLEDPV(or A)GTV-A(or S), said immunoadsorbent comprising a solid support having bound thereto a monoclonal antibody produced by hybridoma cell line A.T.C.C. No. HB8606.

* * * * *

UNITED STATES PATENT AND TRADEMARK OFFICE
CERTIFICATE OF CORRECTION

PATENT NO. : 4,745,182

DATED : May 17, 1988

INVENTOR(S) : Gary H. Cohen & Roselyn J. Eisenberg

It is certified that error appears in the above-identified patent and that said Letters Patent is hereby corrected as shown below:

Table I, Col. 2, line 33, "ACLSPQYQQ..." should be --ACLSPQAYQQ...--.
Col. 2, line 55, "typespecific" should be --type-specific--.
Col. 3, line 67, "34" should be --340--.
Col. 4, line 4, "threefold" should be --three-fold--.
Col. 4, line 6, "culturederived" should be --culture-derived--.
Col. 4, line 49, "(1972)" should be --(1974)--.
Col. 4, line 50, "(1974)" should be --(1972)--.
Col. 4, line 53, "[35S]" should be --[$^{35}$S]--.
Col. 4, line 54, "[2,3-3H]" should be --[2,3-$^{3}$H]--.
Col. 5, line 62, "McAb" should be --MCAb--.
Col. 7, line 5, "125I" should be --$^{125}$I--.
Col. 7, line 11, "DL1-6" should be --DL-6--.
Col. 10, line 58, "anitbody" should be --antibody--.

Signed and Sealed this

Sixteenth Day of March, 1993

Attest:

STEPHEN G. KUNIN

*Attesting Officer*   Acting Commissioner of Patents and Trademarks